United States Patent [19]
Goli et al.

[11] Patent Number: 6,130,325
[45] Date of Patent: Oct. 10, 2000

[54] HUMAN P24 VESICLE PROTEINS

[75] Inventors: Surya K. Goli, Sunnyvale; Olga Bandman, Mountain View, both of Calif.

[73] Assignee: Incyte Pharmaceuticals, Inc., Palo Alto, Calif.

[21] Appl. No.: 08/801,740

[22] Filed: Feb. 14, 1997

[51] Int. Cl.$^7$ .......................... C07H 21/04; C12N 15/63; C12N 1/21
[52] U.S. Cl. .................... 536/23.5; 536/24.31; 536/24.3; 536/24.33; 435/69.1; 435/320.1; 435/252.3
[58] Field of Search ................................ 536/23.5, 24.31, 536/24.3, 24.33; 435/69.1, 252.3, 320.1

[56] References Cited

PUBLICATIONS

"Biochemistry" Lehninger, Worth Publishers, NY 1975 Ch. 34, see especially p. 961.
Hillier, et al., "The WashU–Merck EST Project," *NCBI*, Accession No. AA167650, Dec. 19, 1996.
Hillier, et al., "The WashU–Merck EST Project," *NCBI*, Accession No. N39817, Jan. 22, 1991.
Hillier, et al., "The WashU–NCI Human EST Project," *NCBI*, Accession No. AA479763, Nov. 9, 1997.
National Cancer Institute, "Cancer Genome Anatomy Project," *NCBI*, Accession No. AA469202, Aug. 13, 1997.
Rothman, J.E., "Mechanisms of intracellular protein transport," *Nature*, 372:55–63 (1994).
Stamnes, M., et al., "An integral membrane component of coatomer–coated transport vesicles defines a family of proteins involved in budding," *Proc. Natl. Acad. Sci. USA*, 92:8011–8015 (1995).
Fielder, K., et al., "Bimodal Interaction of Coatomer with the p24 Family of Putative Cargo Receptors," *Science*, 273:1396–1399 (1996).
Schimmöller, F., et al., "The absence of Emp24p, a component of ER–derived COPII–coated vesicles, causes a defect in transport of selected proteins to the Golgi," *EMBO J.*, 14(7):1329–1339 (1995).
Rothman, J., et al., "Protein Sorting by Transport Vesicles," *Science*, 272:227–234 (1996).
Blum, R., et al., "Tmp21 and p24A, Two Type I Proteins Enriched in Pancreatic Microsomal Membranes, Are Members of a Protein Family Involved in Vesicular Trafficking," *J. Biol. Chem.*, 271 (29):17183–17189 (1996).
Gayle, M., et al., "Cloning of a Putative Ligand for the T1/St2 Receptor," *J. Biol. Chem.*, 271 (10):5784–5789 (1996).

*Primary Examiner*—Toni R. Scheiner
*Assistant Examiner*—Nancy A. Johnson
*Attorney, Agent, or Firm*—Leanne C. Price; Lucy J. Billings; Incyte Pharmaceuticals, Inc.

[57] ABSTRACT

The present invention provides two human p24 vesicle trafficking proteins (designated individually as Hp24-1 and Hp24-2 and collectively as Hp24) and polynucleotides which identify and encode Hp24. The invention also provides genetically engineered expression vectors and host cells comprising the nucleic acid sequences encoding Hp24 and a method for producing Hp24. The invention also provides for agonists, antibodies, or antagonists specifically binding Hp24, and their use, in the prevention and treatment of diseases associated with expression of Hp24. Additionally, the invention provides for the use of antisense molecules to polynucleotides encoding Hp24 for the treatment of diseases associated with the expression of Hp24. The invention also provides diagnostic assays which utilize the polynucleotide, or fragments or the complement thereof, and antibodies specifically binding Hp24.

16 Claims, 11 Drawing Sheets

```
                       9              18              27              36              45              54
5'   A  TCC CCT TAC ATN CTN CTA AGA CCC GGT CGG TAG TCG TCG CCC CAG CCC GCC 63              72              81              90              99             108
     GGG GGC GCA GGC CCG AGC CGC GGC CCT CGA GAC GGG ACC GAG AGC ATC ATG GGC
                                                                         M   G 117             126             135             144             153             162
     AGC ACT GTC CCG CGC TCC GGC TNC GTG CTG CTT NTG CTG CTG NTN CTG CGC CGG
      S   T   V   P   R   S   G   X   V   L   L   X   L   L   X   L   R   R 171             180             189             198             207             216
     GCC GAG CAG CCC TGC GGG GCC GAG ATC ACC TTC GAG CTG CCG GAC AAC GCC AAG
      A   E   Q   P   C   G   A   E   I   T   F   E   L   P   D   N   A   K 225             234             243             252             261             270
     CAG TGC TTC CAC GAG GAG GTG GAG CAG GGC GTG AAG TTC TCC CTG GAT TAC CAG
      Q   C   F   H   E   E   V   E   Q   G   V   K   F   S   L   D   Y   Q 279             288             297             306             315             324
     GTC ATC ACT GGA GGC CAC TAC GAT GTT GAC TGC TAT GTA GAG GAC CCC CAG GGG
      V   I   T   G   G   H   Y   D   V   D   C   Y   V   E   D   P   Q   G 333             342             351             360             369             378
     AAC ACC ATC TAC AGA GAA ACG AAG AAG CAG TAC GAC AGC TTC ACG TAC CGG GCT
      N   T   I   Y   R   E   T   K   K   Q   Y   D   S   F   T   Y   R   A 387             396             405             414             423             432
     GAA GTC AAG GGC GTT TAT CAG TTT TGC TTC AGT AAT GAG TTT TCC ACC TTC TCT
      E   V   K   G   V   Y   Q   F   C   F   S   N   E   F   S   T   F   S 441             450             459             468             477             486
     CAC AAG ACC GTC TAC TTT GAC TTT CAA GTG GGC GAT GAG CCT CCC ATT CTC CCA
      H   K   T   V   Y   F   D   F   Q   V   G   D   E   P   P   I   L   P 495             504             513             522             531             540
     GAC ATG GGG AAC AGG GTC ACA GCT CTC ACC CAG NTG GAG TCC GCC TGC GTG ACC
      D   M   G   N   R   V   T   A   L   T   Q   X   E   S   A   C   V   T 549             558             567             576             585             594
     ATC CAT GAG GCT CTG AAA ACG GTG ATT GAC TCC CAG ACG CAT TAC CGG CTG CGG
      I   H   E   A   L   K   T   V   I   D   S   Q   T   H   Y   R   L   R 603             612             621             630             639             648
     GAG GCC CAG GAC CGG GCC CGA GCG GAA GAC CTT AAT AGC CGA GTC TCT TAC TGG
      E   A   Q   D   R   A   R   A   E   D   L   N   S   R   V   S   Y   W 657             666             675             684             693             702
     TCT GTT GGC GAG ACG ATT GCC CTG TTC GTG GTC AGC TTC AGT CAG GTG CTA CTG
      S   V   G   E   T   I   A   L   F   V   V   S   F   S   Q   V   L   L 711             720             729             738             747             756
     TTG AAA AGC TTC TTC ACA GAA AAA CGA CCC ATC AGC AGG GCA GTC CAC TCC TAG
      L   K   S   F   F   T   E   K   R   P   I   S   R   A   V   H   S
```

FIGURE 1A

```
            765         774         783         792         801         810
CCC CGG CAT CCT GCT CTA GGG CCC CTC ATG CCC CAG GCT GGA GCA GTN TTC TAG 819         828         837         846         855         864
GTC ACA GCC TGC TGG GCT GGG TCG CGT AGC CAG GGT GGA GGC AGA ACG ATG CTG 873         882         891         900         909         918
CTG TGG TAG CCC TTT GCC TTT CAT GCC CAT GCT TGA TTC TTG CAA CTC AGC AGC

927
TGA AGG TAA A 3'
```

FIGURE 1B

```
                  9              18              27              36              45              54
5' CGG CTC GAG CGA GGA GTC CAG AGA GGA AAC GCG GAN GAG GAC AAC AGT ACC TGA 63              72              81              90              99             108
   CGC CTC TTT CAG CCC GGG ATC GCC CCA GCA GGG ATG GGC GAC AAG ATC TGG CTG
                                                     M   G   D   K   I   W   L 117             126             135             144             153             162
   CCC TTC CCC GTG CTC CTT CTG GCC GCT CTG CCT CCG GTG CTG CTG CCT GGG GCG
   P   F   P   V   L   L   L   A   A   L   P   P   V   L   L   P   G   A 171             180             189             198             207             216
   GCC GGC TTC ACA CCT TCC CTC GAT AGC GAC TTC ACC TTT ACC CTT CCC GCC GGC
   A   G   F   T   P   S   L   D   S   D   F   T   F   T   L   P   A   G 225             234             243             252             261             270
   CAG AAG GAG TGC TTC TAC CAG CCC ATG CCC CTG AAG GCC TCG CTG GAG ATC GAG
   Q   K   E   C   F   Y   Q   P   M   P   L   K   A   S   L   E   I   E 279             288             297             306             315             324
   TAC CAA GTT TTA GAT GGA GCA GGA TTA GAT ATT GAT TTC CAT CTT GCC TCT CCA
   Y   Q   V   L   D   G   A   G   L   D   I   D   F   H   L   A   S   P 333             342             351             360             369             378
   GAA GGC AAA ACC TTA GTT TTT GAA CAA AGA AAA TCA GAT GGA GTT CAC ACT GTA
   E   G   K   T   L   V   F   E   Q   R   K   S   D   G   V   H   T   V 387             396             405             414             423             432
   GAG ACT GAA GTT GGT GAT TAC ATG TTC TGC TTT GAC AAT ACA TTC AGC ACC ATT
   E   T   E   V   G   D   Y   M   F   C   F   D   N   T   F   S   T   I 441             450             459             468             477             486
   TCT GAG AAG GTG ATT TTC TTT GAA TTA ATC CTG GAT AAT ATG GGA GAA CAG GCA
   S   E   K   V   I   F   F   E   L   I   L   D   N   M   G   E   Q   A 495             504             513             522             531             540
   CAA GAA CAA GAA GAT TGG AAG AAA TAT ATT ACT GGC ACA GAT ATA TTG GAT ATG
   Q   E   Q   E   D   W   K   K   Y   I   T   G   T   D   I   L   D   M 549             558             567             576             585             594
   AAA CTG GAA GAC ATC CTG GAA TCC ATC AAC AGC ATC AAG TCC AGA CTA AGC AAA
   K   L   E   D   I   L   E   S   I   N   S   I   K   S   R   L   S   K 603             612             621             630             639             648
   AGT GGG CAC ATA CAA ATT CTG CTT AGA GCA TTT GAA GCT CGT GAT CGA AAC ATA
   S   G   H   I   Q   I   L   L   R   A   F   E   A   R   D   R   N   I 657             666             675             684             693             702
   CAA GAA AGC AAC TTT GAT AGA GTC AAT TTC TGG TCT ATG GTT AAT TTA GTG GTC
   Q   E   S   N   F   D   R   V   N   F   W   S   M   V   N   L   V   V 711             720             729             738             747             756
   ATG GTG GTG GTG TCA GCC ATT CAA GTT TAT ATG CTG AAG AGT CTG TTT GAA GAT
   M   V   V   V   S   A   I   Q   V   Y   M   L   K   S   L   F   E   D
```

FIGURE 2A

```
        765         774         783         792         801         810
AAG AGG AAA AGT AGA ACT TAA AAC TCC AAA CTA GAG TAC GTA ACA TTG AAA AAT
 K   R   K   S   R   T 819         828         837         846         855         864
GAG GCA TAA AAA TGC AAT AAA CTG TTA CAG TCA AGA CCA TTA ATG GTC TTC TCC 873         882         891
AAA ATA TTT TGA GAT ATA AAA GTA GGG C 3'
```

| | | |
|---|---|---|
| 141 | ESACVTIHEALKTVIDSQTHYRLREAQDRARAEDLNSRVS | 1543121 |
| 155 | KESIETMRTRLERSHQMLTLLRAFEARDRNLQEGNLERVN | GI 1223890 |
| 131 | EEMINELAVAMTAVKHEQEYMEVRERIHRAINDNTNSRVV | GI 1212965 |
| 131 | EEMINELAVAMTAVKHEQEYMEVRERIHRAINDNTNSRVV | GI 1213221 |
| 133 | DSAVRKLSKLTREVKDEQSYIVIRERTHRNTAESTNDRVK | GI 417435 |

| | | |
|---|---|---|
| 181 | YWSVGETIALFVVSFSQVLLLKSFFTEKRPISRAVHS | 1543121 |
| 195 | FWSAVNVAVLLLVAVLQVCTLKRFFQDKRPVP---T | GI 1223890 |
| 171 | LWSFFEALVLVAMTLGQIYYLKRFFEVRRVV | GI 1212965 |
| 171 | LWSFFEALVLVAMTLGQIYYLKRFFEVRRVV | GI 1213221 |
| 173 | WWSIFQLGVVIANSLFQIYYLRRFFEVTSLV | GI 417435 |

| | | | | | |
|---|---|---|---|---|---|
| 153 | L E D I L E S I N S I K S R L S K S G H I Q I L L R A F E A R D R N I Q E S N F | 2506944 |
| 151 | M E D I K E S I E T M R T R L E R S I Q M L T L L R A F E A R D R N L Q E G N L | GI 1223890 |
| 130 | L E E M I N E L A V A M T A V - K H E Q E Y M E V R - - - E R I H R A I N D N T N | GI 1212965 |
| 130 | L E E M I N E L A V A M T A V - K H E Q E Y M E V R - - - E R I H R A I N D N T N | GI 1213221 |
| 132 | L D S A V R K L S K L T R E V - K D E Q S Y I V I R - - - E R T H R N T A E S T N | GI 417435 |
| | | |
| 193 | D R V N F W S M V N L V V M V V S A I Q V Y M L K S L F E D K R K S R T | 2506944 |
| 191 | E R V N F W S A V N V A V L L L V Q V C T L K R F F Q D K R P V P T | GI 1223890 |
| 167 | S R V V L W S F F E A L V L V A M T L G Q I Y Y L K R F F E V R R V V | GI 1212965 |
| 167 | S R V V L W S F F E A L V L V A M T L G Q I Y Y L K R F F E V R R V V | GI 1213221 |
| 169 | D R V K W W S I F Q L G V V I A N S L F Q I Y Y L R R F F E V T S L V | GI 417435 |

FIGURE 4B

| Library | Lib Description | Abun | Pct Abun |
|---|---|---|---|
| PROSNOT05 | prostate, 67 M, match to PROSTUT03 | 2 | 0.1151 |
| LPARNOT02 | parotid gland, 70 M | 2 | 0.0649 |
| COLNNOT13 | colon, ascending, 28 M | 2 | 0.0621 |
| PLACNOM01 | placenta, fetal M, WM | 1 | 0.0580 |
| BLADTUT06 | bladder tumor, carcinoma, 58 M | 1 | 0.0507 |
| PANCNOT01 | pancreas, 29 M | 2 | 0.0428 |
| COLNNOT08 | colon, 60 M | 1 | 0.0426 |
| PROSTUT12 | prostate tumor, 65 M, match to PROSNOT20 | 3 | 0.0420 |
| COLNNOT07 | colon, 60 M | 1 | 0.0409 |
| PROSTUT03 | prostate tumor, 67 M, match to PROSNOT05 | 1 | 0.0352 |
| LNODNOT02 | lymph nodes, 42 F | 1 | 0.0335 |
| TONGTUT01 | tongue tumor, carcinoma, 36 M | 1 | 0.0295 |
| UTRSNOT10 | uterus, endometrium, 50 F | 1 | 0.0292 |
| BRSTTUT02 | breast tumor, 54 F, match to BRSTNOT03 | 2 | 0.0279 |
| SINTNOT13 | small intestine, ileum, ulcerative colitis, 25 F | 1 | 0.0275 |
| BRAINOM03 | brain, 55 M, NORM, WM | 1 | 0.0270 |
| PITUNOT02 | pituitary, 15-75 M/F | 2 | 0.0269 |
| PROSTUT10 | prostate tumor, 66 M, match to PROSNOT15 | 1 | 0.0268 |
| COLNNOT23 | colon, ulcerative colitis, 16 M | 1 | 0.0264 |
| CONUTUT01 | mesentery tumor, sigmoid, 61 F | 2 | 0.0260 |
| LIVRNOM01 | liver, 49 M, WM | 1 | 0.0254 |
| PANCNOT08 | pancreas, 65 F, match to PANCTUT01 | 1 | 0.0254 |
| SPLNFET02 | spleen, fetal M | 2 | 0.0252 |
| LIVSFEM03 | liver/spleen, fetal M, NORM, WM | 1 | 0.0246 |
| PROSTUT04 | prostate tumor, 57 M, match to PROSNOT06 | 2 | 0.0234 |
| UTRPNOM01 | uterus, F, NORM, WM | 1 | 0.0201 |
| BRSTTUT03 | breast tumor, 58 F, match to BRSTNOT05 | 2 | 0.0197 |
| HNT2AGT01 | hNT2 cell line, post-mitotic neurons | 1 | 0.0192 |
| BRAINOT03 | brain, 26 M | 1 | 0.0185 |
| BRSTNOT03 | breast, 54 F, match to BRSTTUT02 | 1 | 0.0147 |
| LATRTUT02 | heart tumor, myoma, 43 M | 1 | 0.0137 |
| SMCANOT01 | smooth muscle cell line, aorta, M | 1 | 0.0136 |
| TESTTUT02 | testicular tumor, 31 M | 1 | 0.0134 |
| PROSNOT16 | prostate, 68 M | 1 | 0.0132 |
| KERANOT02 | keratinocytes, primary cell line, 30 F | 1 | 0.0114 |
| PROSNOT06 | prostate, 57 M, match to PROSTUT04 | 1 | 0.0114 |
| BRSTNOT02 | breast, 55 F, match to BRSTTUT01 | 1 | 0.0111 |
| MELANOM01 | melanocytes, M, NORM, WM | 1 | 0.0096 |
| UCMCL5T01 | mononuclear cells, treated IL-5 | 1 | 0.0084 |
| BRAITUT02 | brain tumor, metastasis, 58 M | 1 | 0.0075 |
| BRAITUT03 | brain tumor, astrocytoma, 17 F | 1 | 0.0074 |
| NGANNOT01 | ganglioneuroma, 9 M | 1 | 0.0073 |

FIGURE 6

HUMAN P24 VESICLE PROTEINS

FIELD OF THE INVENTION

This invention relates to nucleic acid and amino acid sequences of novel human p24 vesicle trafficking proteins and to the use of these sequences in the diagnosis, prevention, and treatment of disorders associated with abnormal vesicle trafficking.

BACKGROUND OF THE INVENTION

Eukaryotic proteins are synthesized within the endoplasmic reticulum (ER), are delivered from the ER to the Golgi complex for post-translational processing and sorting, and are transported from the Golgi to specific intracellular and extracellular destinations. This intracellular and extracellular movement of protein molecules is termed vesicle trafficking. Trafficking is accomplished by the packaging of protein molecules into specialized vesicles which bud from the donor organelle membrane and fuse to the target membrane.

Specialized cell types utilize specific vesicle trafficking routes. For instance, in endocrine glands, hormones and other secreted proteins are delivered to secretory granules for exocytosis through the plasma membrane to the cell exterior. In macrophages, peroxidases and proteases are delivered to lysosomes. In fat and muscle cells, glucose transporters are stored in vesicles which fuse with the plasma membrane in response to insulin stimulation.

Numerous proteins are necessary for the formation, targeting, and fusion of transport vesicles and for the proper sorting of proteins into these vesicles. The vesicle trafficking machinery includes coat proteins which promote the budding of vesicles from donor membranes; vesicle- and target-specific identifiers (v-SNAREs and t-SNAREs) which bind to each other and dock the vesicle to the target membrane; and proteins which bind to SNARE complexes and initiate fusion of the vesicle to the target membrane (SNAPs).

Vesicles in the process of budding from the ER and the Golgi are covered with a protein coat similar to the clathrin coat of endocytotic vesicles. The protein coat is assembled from cytosolic precursor molecules and is confined to budding regions of the organelle membrane. The coat protein (COP)-coated vesicles are uncoated after budding is complete to allow fusion of the vesicle to the donor membrane.

The "pinching off" of the nascent vesicle bud requires a process distinct from coat assembly. Periplasmic fusion, which is membrane fusion initiated from the cytoplasmic side of the bud, may be mediated by integral membrane proteins present in the transport vesicles (Rothman, J. E. (1994) Nature 372:55–63). A membrane protein isolated from COP-coated vesicles of chinese hamster ovary (CHO) cells was found to belong to a family of homologous 24 kdal proteins, known as the p24 family, from ER and Golgi membranes of a broad range of organisms (Stamnes, M. A. et al. (1995) Proc. Natl. Acad. Sci. USA 92:8011–8015).

The p24 family consists of integral membrane proteins which contain a single transmembrane domain located near the C-terminus. All p24 proteins possess a phenylalanine residue located in the cytoplasmic C-terminal portion of the molecule near the transmembrane segment. In all known mammalian p24 proteins, the conserved phenylalanine is followed by two or three basic residues near the C-terminus (Fiedler, K. et al. (1996) Science 273: 1396–1399). p24 proteins bind to various subunits of the COP-coatmer complex, depending on the arrangement of the C-terminal basic residues (Fiedler et al., supra).

A yeast p24 homolog yp24A (also known as Emp24p) isolated from ER-derived COP-coated vesicles is required for the efficient transport of a subset of secretory proteins from the ER to the Golgi (Stamnes et al., supra; Schimmöller, F. et al. (1995) EMBO J. 14:1329–1339). Electron microscopy of yeast cells lacking functional p24A reveals a decrease in steady state vesicle accumulation, which indicates that yp24A is necessary for efficient vesicle budding (Stamnes et al, supra).

Since transport of only a subset of yeast secretory proteins is affected in yp24A mutant cells, Schimmöller, et al. (supra) propose that different yeast p24 homologs may recognize and capture distinct, possibly overlapping sets of proteins into secretory vesicles. Similarly, Stamnes et al. (supra) and Rothman et al. (1996; Science 272:227–234) speculate that p24 homologs may serve as "cargo receptors", selecting proteins for inclusion in budding COP-coated vesicles.

Other members of the evolutionarily related p24 protein family have been cloned from rat and human (Blum, R. et al. (1996) J. Biol. Chem. 271:17183–17189). Rat p24A is abundantly expressed in pancreas, consistent with the proposed role of p24 in the sorting and directing of proteins within the secretory pathway. Furthermore, a protein identified in a human glioblastoma cell line shows significant homology to the p24 family (Gayle, M. A. et al. (1996) J. Biol. Chem. 271:5784–5789). The protein was identified based on its ability to bind to the type I interleukin-1 (IL-1) receptor homolog T1/ST2, yet shows no biological activity in IL-1 or T1/ST2 receptor-based assays (Gayle, supra). Therefore, the putative T1/ST2 binding protein may be another member of the human p24 family.

The etiology of numerous human diseases and disorders can be attributed to defects in the trafficking of proteins to organelles or the cell surface. Defects in the trafficking of membrane-bound receptors and ion channels are associated with cystic fibrosis (cystic fibrosis transmembrane conductance regulator; CFTR), glucose-galactose malabsorption syndrome ($Na^+$/glucose cotransporter), hypercholesterolemia (low-density lipoprotein (LDL) receptor), and forms of diabetes mellitus (insulin receptor). Abnormal hormonal secretion is linked to disorders including diabetes insipidus (vasopressin), hyper- and hypoglycemia (insulin, glucagon), Grave's disease and goiter (thyroid hormone), and Cushing's and Addison's diseases (adrenocorticotropic hormone; ACTH).

Cancer cells secrete excessive amounts of hormones or other biologically active peptides. Disorders related to excessive secretion of biologically active peptides by tumor cells include: fasting hypoglycemia due to increased insulin secretion from insulinoma-islet cell tumors; hypertension due to increased epinephrine and norepinephrine secreted from pheochromocytomas of the adrenal medulla and sympathetic paraganglia; and carcinoid syndrome, which includes abdominal cramps, diarrhea, and valvular heart disease, caused by excessive amounts of vasoactive substances (serotonin, bradykinin, histamine, prostaglandins, and polypeptide hormones) secreted from intestinal tumors. Ectopic synthesis and secretion of biologically active peptides (peptides not expected from a tumor) includes ACTH and vasopressin in lung and pancreatic cancers; parathyroid hormone in lung and bladder cancers; calcitonin in lung and breast cancers; and thyroid-stimulating hormone in medullary thyroid carcinoma.

Polynucleotides encoding novel human p24 vesicle trafficking proteins and the molecules themselves provide a means to investigate vesicle trafficking and secretion under normal and disease conditions. Discovery of novel p24 vesicle trafficking proteins satisfies a need in the art by providing new compositions useful in diagnosing and treating disorders associated with abnormal vesicle trafficking.

SUMMARY OF THE INVENTION

The present invention features two novel human p24 vesicle trafficking proteins, designated individually as Hp24-1 and Hp24-2 and collectively as Hp24, and characterized as having similarity to p24 homologs from yeast, hamster, and human.

Accordingly, the invention features a substantially purified Hp24 proteins Hp24-1 and Hp24-2 having the amino acid sequences shown in SEQ ID NO:1 and SEQ ID NO:3, respectively.

One aspect of the invention features isolated and substantially purified polynucleotides that encode Hp24 proteins Hp24-1 and Hp24-2. In a particular aspect, the polynucleotide is the nucleotide sequence of SEQ ID NO:2 or SEQ ID NO:4.

The invention also relates to a polynucleotide sequence comprising the complement of SEQ ID NO:2, SEQ ID NO:4, or variants thereof. In addition, the invention features polynucleotide sequences which hybridize under stringent conditions to SEQ ID NO:2 or SEQ ID NO:4.

The invention additionally features nucleic acid sequences encoding polypeptides, oligonucleotides, peptide nucleic acids (PNA), fragments, portions or antisense molecules thereof, and expression vectors and host cells comprising polynucleotides that encode Hp24. The present invention also features antibodies which bind specifically to Hp24, and pharmaceutical compositions comprising substantially purified Hp24. The invention also features agonists and antagonists of Hp24. The invention also features methods for treating disorders which are associated with Hp24 and for detecting a polynucleotide which encodes Hp24.

BRIEF DESCRIPTION OF THE FIGURES

FIGS. 1A and 1B show the amino acid sequence (SEQ ID NO:1) and nucleic acid sequence (SEQ ID NO:2) of Hp24-1. The alignment was produced using MACDNASIS PRO software (Hitachi Software Engineering Co., Ltd., San Bruno, Calif.).

FIGS. 2A and 2B show the amino acid sequence (SEQ ID NO:3) and nucleic acid sequence (SEQ ID NO:4) of Hp24-2.

FIGS. 3A and 3B show the amino acid sequence alignments among Hp24-1 (SEQ ID NO:1), putative T1/ST2 binding protein from human (GI 1223890; SEQ ID NO:5), human p24A (GI 1212965; SEQ ID NO:6), rat p24A (GI 1213221; SEQ ID NO:7), and yeast yp24A (GI 417435; SEQ ID NO:8). The alignment was produced using the multisequence alignment program of DNASTAR software (DNASTAR Inc., Madison, Wis.).

FIGS. 4A and 4B show the amino acid sequence alignments among Hp24-2 (SEQ ID NO:3), putative T1/ST2 binding protein from human (GI 1223890; SEQ ID NO:5), human p24A (GI 1212965; SEQ ID NO:6), rat p24A (GI 1213221; SEQ ID NO:7), and yeast yp24A (GI 417435; SEQ ID NO:8).

FIG. 6 shows the northern analysis for SEQ ID NO:2. The northern analysis was produced electronically using the LIFESEQ database (Incyte Pharmaceuticals, Inc., Palo Alto, Calif.).

DESCRIPTION OF THE INVENTION

Figure 5A:
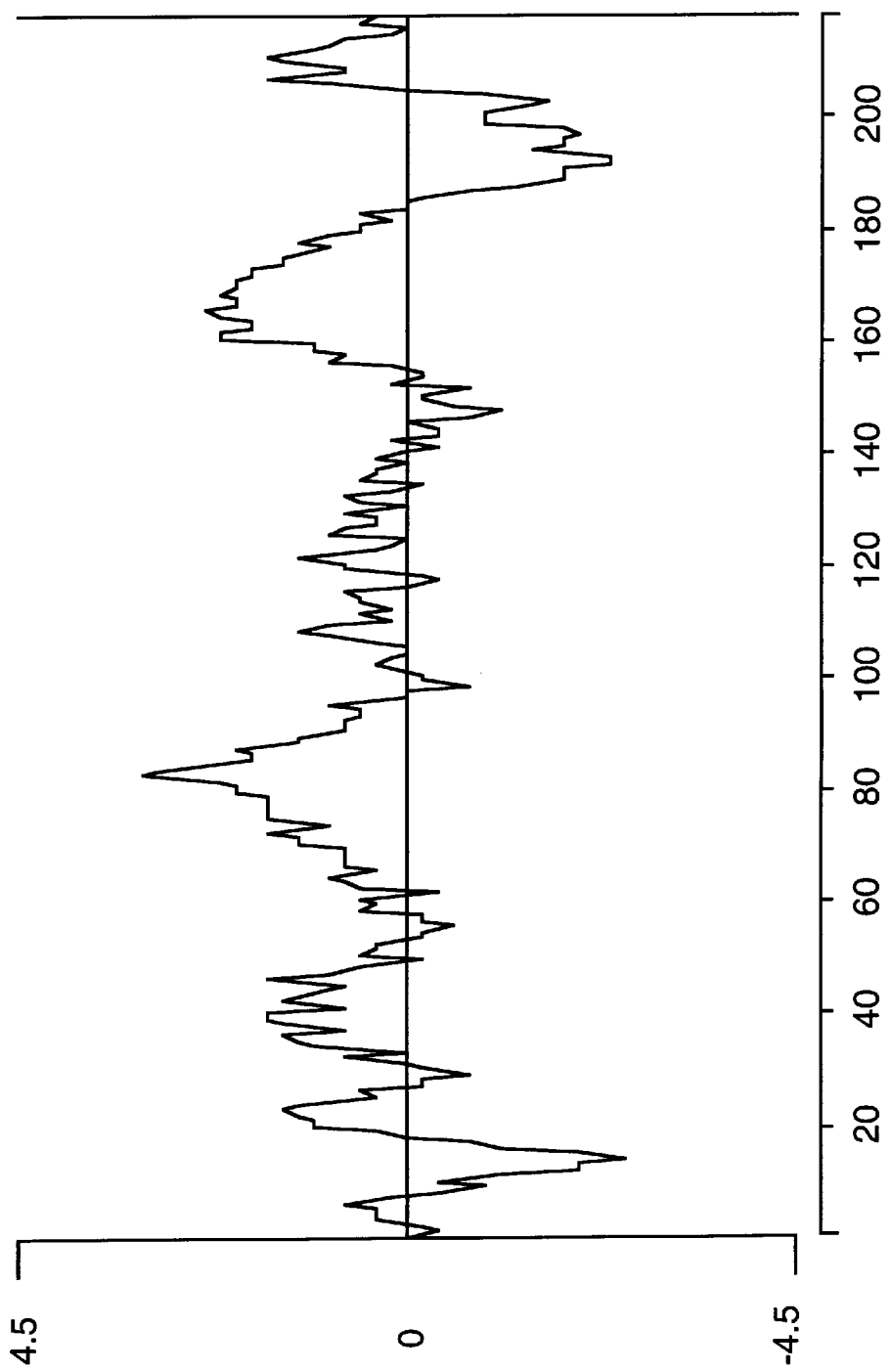
FIGS. 5A and 5B show the Kyte-Doolittle hydrophobicity plots (produced using the PROTEAN protein analysis package of DNASTAR software) for Hp24-1 (SEQ ID NO:1) and Hp24-2 (SEQ ID NO:2) respectively. The positive X axis reflects amino acid position, and the negative Y axis reflects hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

Hp24, as used herein, refers to the amino acid sequences of substantially purified Hp24 obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of Hp24, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic Hp24, or any oligopeptide thereof, to induce a specific immune response in appropriate animals or cells and to bind with specific antibodies.

The term "agonist", as used herein, refers to a molecule which, when bound to Hp24, causes a change in Hp24 which modulates the activity of Hp24. Agonists may include proteins, nucleic acids, carbohydrates, or any other molecules which bind to Hp24.

The terms "antagonist" or "inhibitor", as used herein, refer to a molecule which, when bound to Hp24, blocks or modulates the biological or immunological activity of Hp24. Antagonists and inhibitors may include proteins, nucleic acids, carbohydrates, or any other molecules which bind to Hp24.

The term "modulate", as used herein, refers to a change or an alteration in the biological activity of Hp24. Modulation may be an increase or a decrease in protein activity, a change in binding characteristics, or any other change in the biological, functional or immunological properties of Hp24.

The term "mimetic", as used herein, refers to a molecule, the structure of which is developed from knowledge of the structure of Hp24 or portions thereof and, as such, is able to effect some or all of the actions of p24-like molecules.

The term "derivative", as used herein, refers to the chemical modification of a nucleic acid encoding Hp24 or the encoded Hp24. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human Hp24-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding Hp24 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding Hp24 in a sample and thereby correlates with expression of the transcript from the polynucleotide encoding the protein.

"Alterations" in the polynucleotide of SEQ ID NO:2 or SEQ ID NO:4, as used herein, comprise any alteration in the sequence of polynucleotides encoding Hp24 including deletions, insertions, and point mutations that may be detected using hybridization assays. Included within this definition is the detection of alterations to the genomic DNA sequence which encodes Hp24 (e.g., by alterations in the pattern of restriction fragment length polymorphisms capable of hybridizing to SEQ ID NO:2 or SEQ ID NO:4), the inability of a selected fragment of SEQ ID NO:2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding Hp24 (e.g., using fluorescent in situ hybridization (FISH) to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind Hp24 polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of two novel human p24 vesicle trafficking proteins (Hp24-1 and Hp24-2, collectively referred to as Hp24), the polynucleotides encoding Hp24, and the use of these compositions for the diagnosis, prevention, or treatment of disorders associated with abnormal vesicle trafficking.

Nucleic acids encoding the human Hp24-1 of the present invention were first identified in Incyte Clone 1543121 from the prostate tumor tissue cDNA library (PROSTUT04) through a computer-generated search for amino acid sequence alignments. A consensus sequence, SEQ ID NO:2, was derived from the following overlapping and/or extended nucleic acid sequences: Incyte Clones 642342 (BRSTNOT03); 784732 and 787219 (PROSNOT05); 978556 (BRSTNOT02); 1543121 (PROSTUT04); and 1814352 (PROSNOT20).

Nucleic acids encoding the human Hp24-2 of the present invention were first identified in Incyte Clone 2506944 from the mesentery tumor tissue cDNA library (CONUTUT01) through a computer-generated search for amino acid sequence alignments. A consensus sequence, SEQ ID NO:4, was derived from the following overlapping and/or extended nucleic acid sequences: Incyte Clones 770675 (COLNCRT01); 1650336 (PROSTUT09); 1871164 (SKINBIT01); 1913559 (PROSTUT04); and 2506944 (CONUTUT01).

Figure 3A:
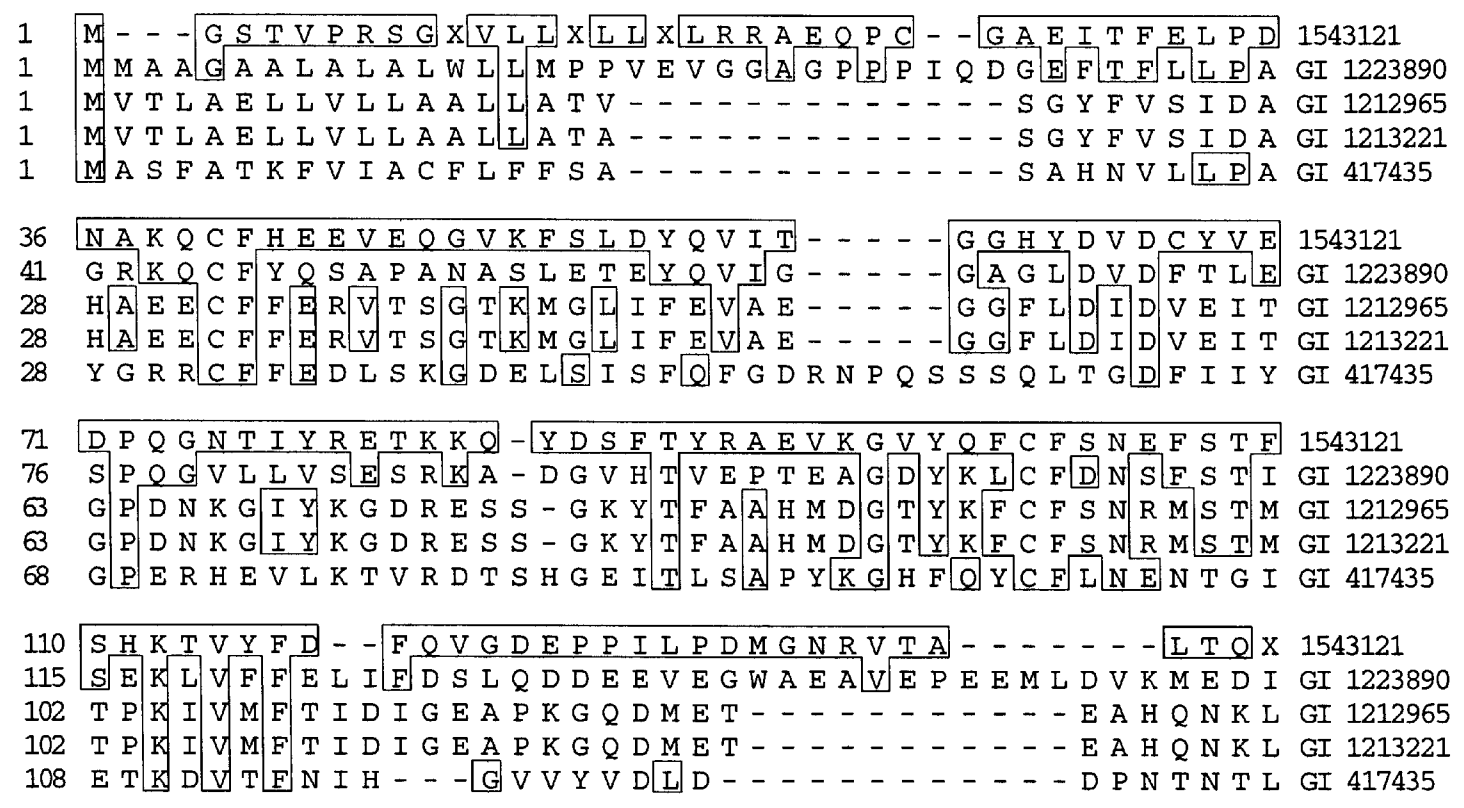

In one embodiment, the invention encompasses a polypeptide comprising the amino acid sequence of SEQ ID NO:1, as shown in FIGS. 1A and 1B. Hp24-1 is 217 amino acids in length and has chemical and structural homology with human T1/ST2 binding protein (GI 1223890; SEQ ID NO:5), human p24A (GI 1212965; SEQ ID NO:6), rat p24A (GI 1213221; SEQ ID NO:7), and yeast yp24A (GI 417435; SEQ ID NO:8). In particular, Hp24-1 and T1/ST2 binding protein share 31% amino acid sequence identity; Hp24-1 and hum-p24A share 31% identity; Hp24-1 and rat p24A share 31% identity; and Hp24-1 and yeast yp24A share 23% identity (FIGS. 3A and 3B). Two cysteines conserved among all the aligned proteins are located at residues $C_{40}$ and $C_{101}$ of SEQ ID NO:1. Hp24-1 contains a potential transmembrane domain between residues $V_{179}$ to $L_{201}$ of SEQ ID NO:1 (FIG. 5A). A phenylalanine which is conserved within the p24 family is located at residue $F_{205}$, near the C-terminal side of the transmembrane domain. Basic amino acids $K_{208}$ and $R_{209}$ follow the conserved phenylalanine near the C-terminus of SEQ ID NO:1. Northern analysis (FIG. 6) shows the expression of this sequence predominantly in libraries prepared from organs and tissues involved in secretion and absorption. Of particular note is the expression of Hp24-1 in prostate, colon, salivary gland, bladder, breast and small intestine tissues associated with tumors and ulcerative colitis.

Figure 4A:
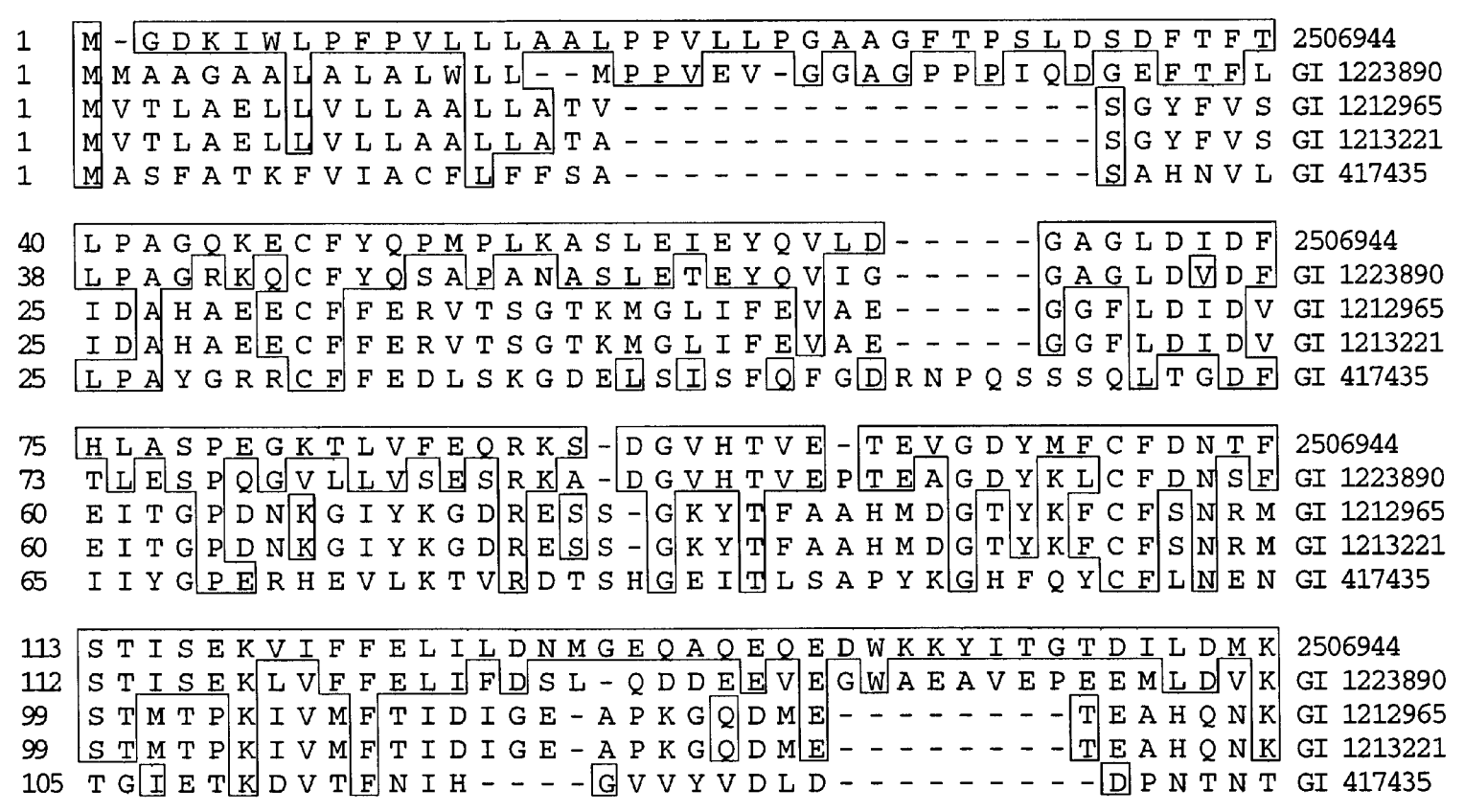
Figure 5B:
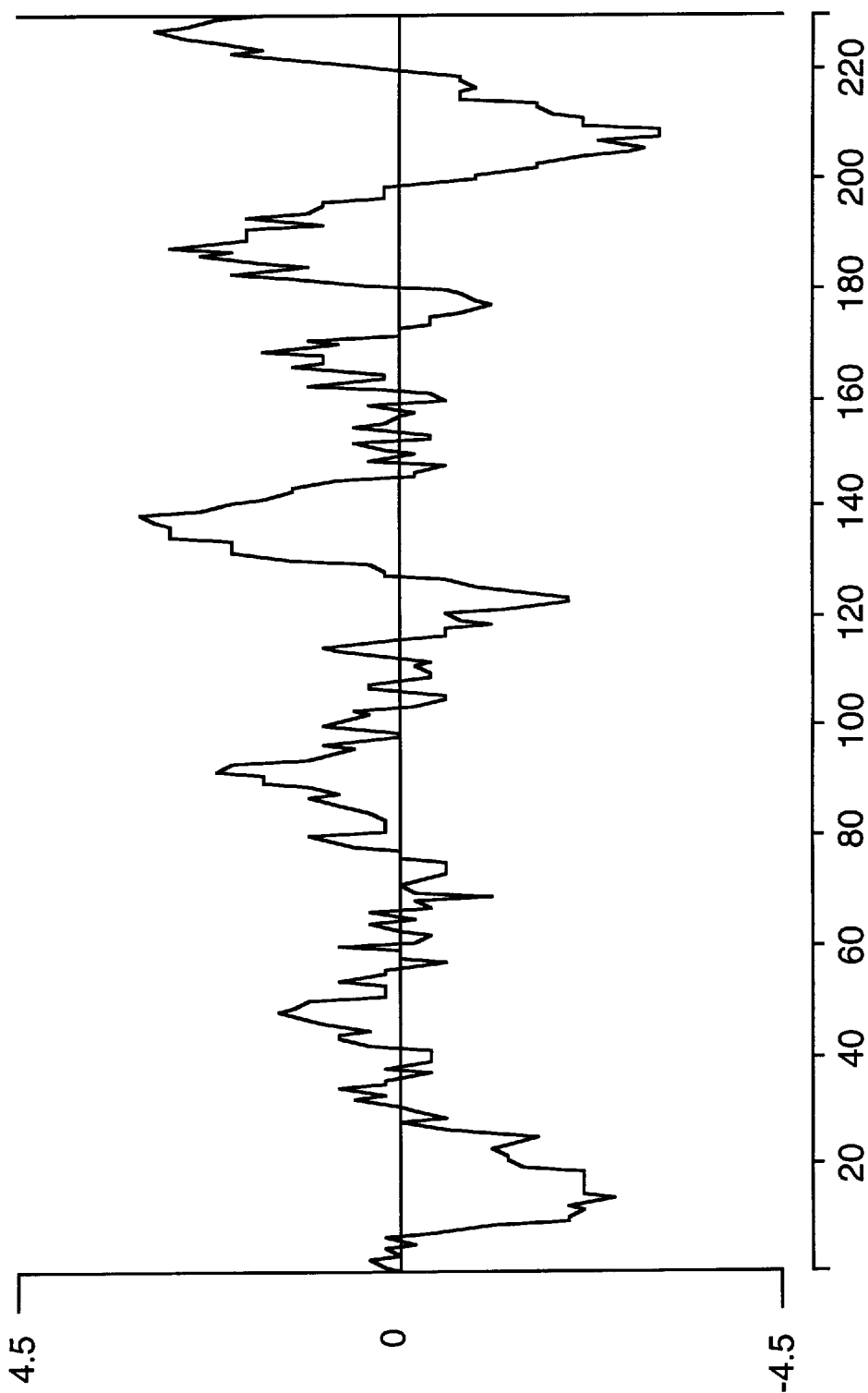

In another embodiment, the invention encompasses a polypeptide comprising the amino acid sequence of SEQ ID NO:3, as shown in FIGS. 2A and 2B. Hp24-2 is 229 amino acids in length and has chemical and structural homology with human T1/ST2 binding protein (GI 1223890; SEQ ID NO:5), human p24A (GI 1212965; SEQ ID NO:6), rat p24A (GI 1213221; SEQ ID NO:7), and yeast yp24A (GI 417435; SEQ ID NO:8). In particular, Hp24-2 and T1/ST2 binding protein share 56% amino acid sequence identity; Hp24-2 and hum-p24A share 28% identity; Hp24-2 and rat p24A share 28% identity; and Hp24-2 and yeast yp24A share 25% identity (FIGS. 4A and 4B). Two cysteines conserved among all the aligned proteins are located at residues $C_{47}$ and $C_{107}$ of SEQ ID NO:3. Hp24-2 contains a potential transmembrane domain between residues $V_{195}$ to $L_{217}$ of SEQ ID NO:3 (FIG. 5B). A phenylalanine which is conserved within the p24 family is located at residue $F_{222}$, near the C-terminal side of the transmembrane domain. Basic amino acids $K_{224}$, $R_{225}$ and $K_{226}$ follow the conserved phenylalanine near the C-terminus of SEQ ID NO:3. Northern analysis shows the expression of this sequence in libraries prepared from organs and tissues involved in secretion and absorption.

The invention also encompasses Hp24 variants. A preferred Hp24 variant is one having at least 80%, and more preferably 90%, amino acid sequence identity to the Hp24 amino acid sequence (SEQ ID NO:1 or SEQ ID NO:3). A most preferred Hp24 variant is one having at least 95% amino acid sequence identity to SEQ ID NO:1 or SEQ ID NO:3.

The invention also encompasses polynucleotides which encode Hp24. Accordingly, any nucleic acid sequence which encodes the amino acid sequence of Hp24 can be used to generate recombinant molecules which express Hp24. In a particular embodiment, the invention encompasses the polynucleotide comprising the nucleic acid sequence of SEQ ID NO:2 or SEQ ID NO:4 as shown in FIGS. 1A and 1B and FIGS. 2A and 2B, respectively.

It will be appreciated by those skilled in the art that as a result of the degeneracy of the genetic code, a multitude of nucleotide sequences encoding Hp24, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring Hp24, and all such variations are to be considered as being specifically disclosed.

Although nucleotide sequences which encode Hp24 and its variants are preferably capable of hybridizing to the nucleotide sequence of the naturally occurring Hp24 under appropriately selected conditions of stringency, it may be advantageous to produce nucleotide sequences encoding Hp24 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding Hp24 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode Hp24 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding Hp24 or any portion thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding Hp24 which are encompassed by the invention include deletions, insertions, or substitutions of different nucleotides resulting in a polynucleotide that encodes the same or a functionally equivalent Hp24. The encoded protein may also contain deletions, insertions, or substitutions of amino acid residues which produce a silent change and result in a functionally equivalent Hp24. Deliberate amino acid substitutions may be made on the basis of similarity in polarity, charge, solubility, hydrophobicity, hydrophilicity, and/or the amphipathic nature of the residues as long as the biological activity of Hp24 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding Hp24. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the Hamilton MICRO-LAB 2200 (Hamilton, Reno, Nev.), Peltier thermal cycler (PTC200; MJ Research, Watertown, Mass.) and the ABI 377 DNA sequencers (Perkin Elmer).

The nucleic acid sequences encoding Hp24 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTER FINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode Hp24, or fusion proteins or functional equivalents thereof, may be used in recombinant DNA molecules to direct expression of Hp24 in appropriate host cells. Due to the inherent degeneracy of the genetic code, other DNA sequences which encode substantially the same or a functionally equivalent amino acid sequence may be produced and these sequences may be used to clone and express Hp24.

As will be understood by those of skill in the art, it may be advantageous to produce Hp24-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter Hp24 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding Hp24 may be ligated to a heterologous sequence to encode a fusion protein. For example, to screen peptide libraries for inhibitors of Hp24 activity, it may be useful to encode a chimeric Hp24 protein that can be recognized by a commercially available antibody. A fusion protein may also be engineered to contain a cleavage site located between the Hp24 encoding sequence and the heterologous protein sequence, so that Hp24 may be cleaved and purified away from the heterologous moiety.

In another embodiment, sequences encoding Hp24 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of Hp24, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of Hp24, or any part thereof, may be altered during direct synthesis and/or combined using chemical methods with sequences from other proteins, or any part thereof, to produce a variant polypeptide.

In order to express a biologically active Hp24, the nucleotide sequences encoding Hp24 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding Hp24 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding Hp24. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding Hp24, vectors based on SV40 or EBV may be used with an appropriate selectable marker.

In bacterial systems, a number of expression vectors may be selected depending upon the use intended for Hp24. For example, when large quantities of Hp24 are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding Hp24 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding Hp24 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express Hp24. For example, in one such system, *Autographa californica* nuclear polyhedrosis virus (AcNPV) is used as a vector to express foreign genes in *Spodoptera frugiperda* cells or in Trichoplusia larvae. The sequences encoding Hp24 may be cloned into a non-essential region of the virus, such as the polyhedrin gene, and placed under control of the polyhedrin promoter. Successful insertion of Hp24 will render the polyhedrin gene inactive and produce recombinant virus lacking coat protein. The recombinant viruses may then be used to infect, for example, *S. frugiperda* cells or Trichoplusia larvae in which Hp24 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding Hp24 may be ligated into an adenovirus transcription/translation complex consisting of the late promoter and tripartite leader sequence. Insertion in a non-essential E1 or E3 region of the viral genome may be used to obtain a viable virus which is capable of expressing Hp24 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding Hp24. Such signals include the ATG initiation codon and adjacent sequences. In cases where sequences encoding Hp24, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express Hp24 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding Hp24 is inserted within a marker gene sequence, recombinant cells containing sequences encoding Hp24 can be identified by the absence of marker gene function. Alternatively, a marker gene can be placed in tandem with a sequence encoding Hp24 under the control of a single promoter. Expression of the marker gene in response to induction or selection usually indicates expression of the tandem gene as well.

Alternatively, host cells which contain the nucleic acid sequence encoding Hp24 and express Hp24 may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding Hp24 can be detected by DNA—DNA or DNA-RNA hybridization or amplification using probes or portions or fragments of polynucleotides encoding Hp24. Nucleic acid amplification based assays involve the use of oligonucleotides or oligomers based on the sequences encoding Hp24 to detect transformants containing DNA or RNA encoding Hp24. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of Hp24, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on Hp24 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding Hp24 include oligolabeling, nick translation, end-labeling or PCR amplification using a labeled nucleotide. Alternatively, the sequences encoding Hp24, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., Cleveland, Ohio)). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding Hp24 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode Hp24 may be designed to contain signal sequences which direct secretion of Hp24 through a prokaryotic or eukaryotic cell membrane. Other recombinant constructions may be used to join sequences encoding Hp24 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and Hp24 may be used to facilitate purification. One such expression vector provides for expression of a fusion protein containing Hp24 and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying Hp24 from the fusion protein. A discussion of vectors which contain fusion proteins is provided in Kroll, D. J. et al. (1993; DNA Cell Biol. 12:441–453).

In addition to recombinant production, fragments of Hp24 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of Hp24 may be chemically synthesized separately and combined using chemical methods to produce the full length molecule.

THERAPEUTICS

Chemical and structural homology exists among Hp24, human T1/ST2 binding protein, human p24A, rat p24A, and yeast yp24A. In addition, Hp24 is expressed in glands and tissues involved in secretion and absorption. Hp24 therefore appears to have a role in vesicle trafficking, and thus may be associated with disorders of abnormal vesicle trafficking, including endocrine, secretory, inflammatory, and gastrointestinal disorders, and in the development of cancers, particularly those involving secretory and gastrointestinal tissues.

Therefore, in one embodiment, Hp24 or a fragment or derivative thereof may be administered to a subject to treat disorders associated with abnormal vesicle trafficking. Such disorders may include, but are not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, Addison's disease; gastrointestinal disorders including ulcerative colitis, gastric and duodenal ulcers; and other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections.

In another embodiment, a vector capable of expressing Hp24, or a fragment or a derivative thereof, may also be administered to a subject to treat any disorder associated with abnormal vesicle trafficking, including those listed above.

Cancer cells secrete excessive amounts of hormones or other biologically active peptides. Therefore, in another embodiment, antagonists or inhibitors of Hp24 may be administered to a subject to treat or prevent cancer, including, but not limited to, cancers of glands, tissues, and organs involved in secretion or absorption, including prostate, pancreas, lung, tongue, brain, breast, bladder, adrenal gland, thyroid, liver, uterus, kidney, testes, and organs of the gastrointestinal tract including small intestine, colon, rectum, and stomach. In particular, antibodies which are specific for Hp24 may be used directly as an antagonist, or indirectly as a targeting or delivery mechanism for bringing a pharmaceutical agent to cells or tissue which express Hp24.

In another embodiment, a vector expressing antisense of the polynucleotide encoding Hp24 may be administered to a subject to treat or prevent cancer, including those listed above.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of Hp24 may be produced using methods which are generally known in the art. In particular, purified Hp24 may be used to produce antibodies or to screen libraries of pharmaceutical agents to identify those which specifically bind Hp24.

Antibodies specific for Hp24 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with Hp24 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to Hp24 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of Hp24 amino acids may be fused with those of another protein such as keyhole limpet hemocyanin and antibody produced against the chimeric molecule.

Monoclonal antibodies to Hp24 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce Hp24-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for Hp24 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Hp24 and its specific antibody. A two-site, monoclonal-based immunoassay utilizing monoclonal antibodies reactive to two non-interfering Hp24 epitopes is preferred, but a competitive binding assay may also be employed (Maddox, supra).

In another embodiment of the invention, the polynucleotides encoding Hp24, or any fragment thereof, or antisense molecules, may be used for therapeutic purposes. In one aspect, antisense to the polynucleotide encoding Hp24 may be used in situations in which it would be desirable to block the transcription of the mRNA. In particular, cells may be transformed with sequences complementary to polynucleotides encoding Hp24. Thus, antisense molecules may be used to modulate Hp24 activity, or to achieve regulation of gene function. Such technology is now well known in the art, and sense or antisense oligomers or larger fragments, can be designed from various locations along the coding or control regions of sequences encoding Hp24.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding Hp24. These techniques are described both in Sambrook et al. (supra) and in Ausubel et al. (supra).

Genes encoding Hp24 can be turned off by transforming a cell or tissue with expression vectors which express high levels of a polynucleotide or fragment thereof which encodes Hp24. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding Hp24, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding Hp24.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding Hp24. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of Hp24, antibodies to Hp24, mimetics, agonists, antagonists, or inhibitors of Hp24. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of Hp24, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Hp24 or fragments thereof, antibodies of Hp24, agonists, antagonists or inhibitors of Hp24, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind Hp24 may be used for the diagnosis of conditions or diseases characterized by expression of Hp24, or in assays to monitor patients being treated with Hp24, agonists, antagonists or inhibitors. The antibodies useful for diagnostic purposes may be prepared in the same manner as those described above for therapeutics. Diagnostic assays for Hp24 include methods which utilize the antibody and a label to detect Hp24 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring Hp24 are known in the art and provide a basis for diagnosing altered or abnormal levels of Hp24 expression. Normal or standard values for Hp24 expression are established by combining body fluids or cell extracts taken from normal mammalian subjects, preferably human, with antibody to $Hp^{24}$ under conditions suitable for complex formation. The amount of standard complex formation may be quantified by various methods, preferably by photometric means. Quantities of Hp24 expressed in subject samples from biopsied tissues are compared with the standard values. Deviation between standard and subject values establishes the parameters for diagnosing disease.

In another embodiment of the invention, the polynucleotides encoding Hp24 may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of Hp24 may be correlated with disease. The diagnostic assay may be used to distinguish between absence, presence, and excess expression of Hp24, and to monitor regulation of Hp24 levels during therapeutic intervention.

In one aspect, hybridization with PCR probes which are capable of detecting polynucleotide sequences, including genomic sequences, encoding Hp24 or closely related molecules, may be used to identify nucleic acid sequences which encode Hp24. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding Hp24, alleles, or related sequences.

Probes may also be used for the detection of related sequences, and should preferably contain at least 50% of the nucleotides from any of the Hp24 encoding sequences. The hybridization probes of the subject invention may be DNA or RNA and derived from the nucleotide sequence of SEQ ID NO:2 or SEQ ID NO:4 or from genomic sequence including promoter, enhancer elements, and introns of the naturally occurring Hp24.

Means for producing specific hybridization probes for DNAs encoding Hp24 include the cloning of nucleic acid sequences encoding Hp24 or Hp24 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding Hp24 may be used for the diagnosis of disorders which are associated with expression of Hp24. Examples of such disorders include cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including gastric and duodenal ulcers and ulcerative colitis; cancers of glands, tissues, and organs involved in secretion or absorption, including prostate, pancreas, lung, tongue, brain, breast, bladder, adrenal gland, thyroid, liver, uterus, kidney, testes, and organs of the gastrointestinal tract including small intestine, colon, rectum, and stomach; AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; viral, bacterial, fungal, helminth, and protozoal infections. The polynucleotide sequences encoding Hp24 may be used in Southern or northern analysis, dot blot, or other membrane-based technologies; in PCR technologies; or in dip stick, pin, ELISA or chip assays utilizing fluids or tissues from patient biopsies to detect altered Hp24 expression. Such qualitative or quantitative methods are well known in the art.

In a particular aspect, the nucleotide sequences encoding Hp24 may be useful in assays that detect activation or induction of various cancers, particularly those mentioned above. The nucleotide sequences encoding Hp24 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding Hp24 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of Hp24, a normal or standard profile for expression is established. This may be accomplished by combining body fluids or cell extracts taken from normal subjects, either animal or human, with a sequence, or a fragment thereof, which encodes Hp24, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding Hp24 may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of Hp24 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode Hp24 may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding Hp24 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, Hp24, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between Hp24 and the agent being tested, may be measured.

Another technique for drug screening which may be used provides for high throughput screening of compounds having suitable binding affinity to the protein of interest as described in published PCT application WO84/03564. In this method, as applied to Hp24 large numbers of different small test compounds are synthesized on a solid substrate, such as plastic pins or some other surface. The test compounds are reacted with Hp24, or fragments thereof, and washed. Bound Hp24 is then detected by methods well known in the art. Purified Hp24 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding Hp24 specifically compete with a test compound for binding Hp24. In this manner, the antibodies can be used to detect the presence of any peptide which shares one or more antigenic determinants with Hp24.

In additional embodiments, the nucleotide sequences which encode Hp24 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

PROSTUT04

The PROSTUT04 cDNA library was constructed from prostate tumor tissue of a 57-year-old Caucasian male. Surgery included a radical prostatectomy, removal of both testes and excision of regional lymph nodes. The pathology report indicated an adenocarcinoma (Gleason grade 3+3) in both the left and right periphery of the prostate. Perineural invasion was present, as was involvement of periprostatic tissue. A single right pelvic lymph node, and the right and left apical surgical margins were positive for tumor. The seminal vesicles were negative for tumor. The patient history reported a previous tonsillectomy with adenoidectomy, appendectomy and a benign neoplasm of the large bowel. The patient was taking insulin for type I diabetes. The patient's family history included a malignant neoplasm of the prostate in the patient's father and type I diabetes without complications in the mother.

The frozen tissue was homogenized and lysed using a Polytron-PT 3000 homogenizer (Brinkmann Instruments, Inc. Westbury, N.Y.) in guanidinium isothiocyanate solution. After adding 1.0 ml of 2M of sodium acetate to the lysate, it was extracted once with phenol chloroform at pH 5.5 and once with acid phenol at pH 4.7. RNA was precipitated twice with an equal volume of isopropanol. The RNA pellet was resuspended in DEPC-treated water and DNase treated for 50 min at 37° C. The reaction was stopped with an equal volume of acid phenol. RNA was precipitated using 0.3 M sodium acetate and 2.5 volumes of ethanol and resuspended in DEPC-treated water. The mRNA was isolated with the Qiagen OLIGOTEX kit (QIAGEN Inc. Chatsworth, Calif.) and used to construct the cDNA library.

The mRNA was handled according to the recommended protocols in the SUPERSCRIPT (Cat. #18248-013; Gibco/BRL, Gaithersberg, Md.). cDNAs were fractionated on a SEPHAROSE CL4B column (Cat. #275105, Pharmacia), and those cDNAs exceeding 400 bp were ligated into PSPORT1. The plasmid PSPORT1 was subsequently transformed into DH5α™ competent cells (Cat. #18258-012, Gibco/BRL).

CONUTUT01

The CONUTUT01 cDNA library was constructed from sigmoid mesentery tumor tissue removed from a 61-year old female during abdominal excision of multiple tumors. Pathology indicated a metastatic grade 4 malignant mixed mullerian tumor present in the sigmoid mesentery at two sites. Pathology of adjacent tissues indicated a grade 4 malignant mixed mullerian tumor, heterologous type of the uterus forming a firm, infiltrating mass throughout the myometrium and involving the serosal surface. The heterologous elements of the tumor consisted of rhabdomyoblasts and immature cartilage. The tumor also involved the lower uterine segment and extended into the cervical wall. Extensive lymphatic and vascular permeation was identified in the myometrium and cervical wall. A single (of 7) right common iliac and a single (of 7) right external iliac lymph nodes were identified with metastatic grade 4 malignant mixed mullerian tumor cells. Estrogen and progesterone receptor studies were positive.

The frozen tissue was homogenized and lysed in Trizol reagent (1 gm tissue/10 ml Trizol; Cat. #10296-028; Gibco/BRL) using a Polytron PT-3000 homogenizer (Brinkmann Instruments, Westbury, N.Y.). After a brief incubation on ice, chloroform was added (1:5 v/v), and the lysate was centrifuged. The upper chloroform layer was removed to a fresh tube, and the RNA was extracted with isopropanol, resuspended in DEPC-treated water, and DNase treated for 25 min at 37° C. The RNA was extracted twice more with acid phenol-chloroform pH 4.7 and precipitated using 0.3M sodium acetate and 2.5 volumes ethanol. The mRNA was isolated with the Qiagen OLIGOTEX kit (QIAGEN, Inc.) and used to construct the cDNA library.

The mRNA was handled according to the recommended protocols in the SUPERSCRIPT plasmid system for cDNA synthesis and plasmid cloning (Cat. #18248-013, Gibco/BRL). CONUTUT01 cDNAs were fractionated on a SEPHAROSE CL4B column (Cat. #275105-01; Pharmacia), and those cDNAs exceeding 400 bp were ligated into pINCY 1. The plasmid pINCY 1 was subsequently transformed into DH5α competent cells (Cat. #18258-012; Gibco/BRL).

II Isolation and Sequencing of cDNA Clones

Plasmid DNA was released from the cells and purified using the R.E.A.L. PREP 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, *J. Mol. Biol.* 94:441f), using a Hamilton MICROLAB 2200 (Hamilton, Reno, Nev.) in combination with Peltier thermal cyclers (PTC200 from MJ Research, Watertown, Mass.) and Applied Biosystems 377 DNA sequencing systems; and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding Hp24 occurs. Abundance and percent abundance are also reported. Abundance directly reflects the number of times a particular transcript is represented in a cDNA library, and percent abundance is abundance divided by the total number of sequences examined in the cDNA library.

V Extension of Hp24-Encoding Polynucleotides to Full Length or to Recover Regulatory Sequences Full length Hp24-encoding nucleic acid sequence (SEQ ID NO:2 or SEQ ID NO:4) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba I, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, or the blots are exposed to a Phosphoimager cassette (Molecular Dynamics, Sunnyvale, Calif.), hybridization patterns are compared visually.

VII Antisense Molecules

Antisense molecules to the Hp24-encoding sequence, or any part thereof, is used to inhibit in vivo or in vitro expression of naturally occurring Hp24. Although use of antisense oligonucleotides, comprising about 20 base-pairs, is specifically described, essentially the same procedure is used with larger cDNA fragments. An oligonucleotide based on the coding sequences of Hp24, as shown in FIGS. 1A and 1B and FIGS. 2A and 2B, is used to inhibit expression of naturally occurring Hp24. The complementary oligonucleotide is designed from the most unique 5' sequence as shown in FIGS. 1A and 1B and FIGS. 2A and 2B and used either to inhibit transcription by preventing promoter binding to the upstream nontranslated sequence or translation of an Hp24-encoding transcript by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIGS. 1A and 1B and FIGS. 2A and 2B.

VIII Expression of Hp24

Expression of Hp24 is accomplished by subcloning the cDNAs into appropriate vectors and transforming the vectors into host cells. In this case, the cloning vector, pSport, previously used for the generation of the cDNA library is used to express Hp24 in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein.

IX Demonstration of Hp24 Activity

Hp24 can be expressed in a mammalian cell line such as CHO by transforming with an eukaryotic expression vector encoding Hp24. Eukaryotic expression vectors are commercially available, and the techniques to introduce them into cells are well known to those skilled in the art. The vesicular localization of Hp24 is examined using microscopy and a fluorescent antibody specific for extra-membrane portions of Hp24. The number, arrangement, specificity and pathway of vesicles containing Hp24 is examined. The search includes various cellular components such as ER, Golgi bodies, peroxisomes, lysosomes, and the plasmalemma and produces the information important to disrupt vesicular processes in disease intervention, for example, in tumors.

X Production of Hp24 Specific Antibodies

Hp24 that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring Hp24 Using Specific Antibodies

Naturally occurring or recombinant Hp24 is substantially purified by immunoaffinity chromatography using antibodies specific for Hp24. An immunoaffinity column is constructed by covalently coupling Hp24 antibody to an activated chromatographic resin, such as CnBr-activated SEPHAROSE (Pharmacia & Upjohn). After the coupling, the resin is blocked and washed according to the manufacturer's instructions.

Media containing Hp24 is passed over the immunoaffinity column, and the column is washed under conditions that allow the preferential absorbance of Hp24 (e.g., high ionic strength buffers in the presence of detergent). The column is eluted under conditions that disrupt antibody/Hp24 binding (e.g., a buffer of pH 2–3 or a high concentration of a chaotrope, such as urea or thiocyanate ion), and Hp24 is collected.

XII Identification of Molecules Which Interact with Hp24

Hp24 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled Hp24, washed and any wells with labeled Hp24 complex are assayed. Data obtained using different concentrations of Hp24 are used to calculate values for the number, affinity, and association of Hp24 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A hybridization probe consisting of the polynucleotide sequence of claim 1 and a detectable label.

3. An isolated and purified polynucleotide sequence comprising SEQ ID NO:2.

4. An isolated and purified polynucleotide sequence which is completely complementary to the polynucleotide sequence of claim 1.

5. A hybridization probe consisting of the isolated and purified polynucleotide sequence of claim 4 and a detectable label.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:
 a) culturing the host cell of claim 7 under conditions suitable for the expression of the polypeptide; and
 b) recovering the polypeptide from the host cell culture.

9. An isolated and purified polynucleotide sequence encoding a polypeptide comprising the amino acid sequence of SEQ ID NO:3.

10. A hybridization probe consisting of the polynucleotide sequence of claim 9 and a detectable label.

11. An isolated and purified polynucleotide sequence comprising SEQ ID NO:4.

12. An isolated and purified polynucleotide sequence which is completely complementary to the isolated and purifiedbpolynucleotide sequence of claim 9.

13. A hybridization probe consisting of the polynucleotide sequence of claim 12 and a detectable label.

14. An expression vector containing the polynucleotide sequence of claim 9.

15. A host cell containing the expression vector of claim 14.

16. A method for producing a polypeptide comprising the amino acid sequence of SEQ ID NO:3, the method comprising the steps of:
 a) culturing the host cell of claim 15 under conditions suitable for the expression of the polypeptide; and
 b) recovering the polypeptide from the host cell culture.

* * * * *

UNITED STATES PATENT AND TRADEMARK OFFICE
CERTIFICATE OF CORRECTION

PATENT NO. : 6,130,325
DATED : October 10, 2000
INVENTOR(S) : Goli et al.

It is certified that error appears in the above-identified patent and that said Letters Patent is hereby corrected as shown below:

Column 46,
Line 48, delete "purifiedbpolynucleotide" and insert -- purified polynucleotide --.
Lines 38 and 54, delete "claim 4" and insert -- claim 14 --.

Signed and Sealed this

First Day of January, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 217 amino acids
      (B) TYPE: amino acid
      (C) STRANDEDNESS: single
      (D) TOPOLOGY: linear (vii) IMMEDIATE SOURCE:
      (A) LIBRARY: Consensus
      (B) CLONE: Consensus (xi) SEQUENCE DESCRIPTION: SEQ ID NO: 1:

```
Met Gly Ser Thr Val Pro Arg Ser Gly Xaa Val Leu Leu Xaa Leu Leu
 1               5                  10                  15

Xaa Leu Arg Arg Ala Glu Gln Pro Cys Gly Ala Glu Ile Thr Phe Glu
                20                  25                  30

Leu Pro Asp Asn Ala Lys Gln Cys Phe His Glu Glu Val Glu Gln Gly
                35                  40                  45

Val Lys Phe Ser Leu Asp Tyr Gln Val Ile Thr Gly Gly His Tyr Asp
50                  55                  60

Val Asp Cys Tyr Val Glu Asp Pro Gln Gly Asn Thr Ile Tyr Arg Glu
65                  70                  75                  80

Thr Lys Lys Gln Tyr Asp Ser Phe Thr Tyr Arg Ala Glu Val Lys Gly
                85                  90                  95

Val Tyr Gln Phe Cys Phe Ser Asn Glu Phe Ser Thr Phe Ser His Lys
                100                 105                 110

Thr Val Tyr Phe Asp Phe Gln Val Gly Asp Glu Pro Pro Ile Leu Pro
                115                 120                 125

Asp Met Gly Asn Arg Val Thr Ala Leu Thr Gln Xaa Glu Ser Ala Cys
130                 135                 140

Val Thr Ile His Glu Ala Leu Lys Thr Val Ile Asp Ser Gln Thr His
145                 150                 155                 160

Tyr Arg Leu Arg Glu Ala Gln Asp Arg Ala Arg Ala Glu Asp Leu Asn
                165                 170                 175

Ser Arg Val Ser Tyr Trp Ser Val Gly Glu Thr Ile Ala Leu Phe Val
                180                 185                 190

Val Ser Phe Ser Gln Val Leu Leu Leu Lys Ser Phe Phe Thr Glu Lys
                195                 200                 205

Arg Pro Ile Ser Arg Ala Val His Ser
210                 215
```

(2) INFORMATION FOR SEQ ID NO: 2:

(i) SEQUENCE CHARACTERISTICS:
      (A) LENGTH: 926 base pairs
      (B) TYPE: nucleic acid
      (C) STRANDEDNESS: single
      (D) TOPOLOGY: linear (vii) IMMEDIATE SOURCE:
      (A) LIBRARY: Consensus
      (B) CLONE: Consensus (xi) SEQUENCE DESCRIPTION: SEQ ID NO: 2:

```
ATCCCCTTAC ATNCTNCTAA GACCCGGTCG GTAGTCGTCG CCCCAGCCCG CCGGGGGCGC      60

AGGCCCGAGC CGCGGCCCTC GAGACGGGAC CGAGAGCATC ATGGGCAGCA CTGTCCCGCG     120

CTCCGGCTNC GTGCTGCTTN TGCTGCTGNT NCTGCGCCGG GCCGAGCAGC CCTGCGGGGC    180

CGAGATCACC TTCGAGCTGC CGGACAACGC CAAGCAGTGC TTCCACGAGG AGGTGGAGCA    240

GGGCGTGAAG TTCTCCCTGG ATTACCAGGT CATCACTGGA GGCCACTACG ATGTTGACTG    300

CTATGTAGAG GACCCCCAGG GGAACACCAT CTACAGAGAA ACGAAGAAGC AGTACGACAG    360

CTTCACGTAC CGGGCTGAAG TCAAGGGCGT TTATCAGTTT TGCTTCAGTA ATGAGTTTTC    420

CACCTTCTCT CACAAGACCG TCTACTTTGA CTTTCAAGTG GGCGATGAGC CTCCCATTCT    480

CCCAGACATG GGAACAGGG TCACAGCTCT CACCCAGNTG GAGTCCGCCT GCGTGACCAT     540

CCATGAGGCT CTGAAAACGG TGATTGACTC CCAGACGCAT TACCGGCTGC GGGAGGCCCA    600

GGACCGGGCC CGAGCGGAAG ACCTTAATAG CCGAGTCTCT TACTGGTCTG TTGGCGAGAC    660

GATTGCCCTG TTCGTGGTCA GCTTCAGTCA GGTGCTACTG TTGAAAAGCT TCTTCACAGA    720

AAAACGACCC ATCAGCAGGG CAGTCCACTC CTAGCCCCGG CATCCTGCTC TAGGGCCCCT    780

CATGCCCCAG GCTGGAGCAG TNTTCTAGGT CACAGCCTGC TGGGCTGGGT CGCGTAGCCA    840

GGGTGGAGGC AGAACGATGC TGCTGTGGTA GCCCTTTGCC TTTCATGCCC ATGCTTGATT    900

CTTGCAACTC AGCAGCTGAA GGTAAA                                         926
```

(2) INFORMATION FOR SEQ ID NO: 3:

(i) SEQUENCE CHARACTERISTICS:
        (A) LENGTH: 229 amino acids
        (B) TYPE: amino acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO: 3:

```
Met Gly Asp Lys Ile Trp Leu Pro Phe Pro Val Leu Leu Ala Ala
 1               5                  10                  15

Leu Pro Pro Val Leu Pro Gly Ala Ala Gly Phe Thr Pro Ser Leu
             20                  25                  30

Asp Ser Asp Phe Thr Phe Thr Leu Pro Ala Gly Gln Lys Glu Cys Phe
             35                  40                  45

Tyr Gln Pro Met Pro Leu Lys Ala Ser Leu Glu Ile Glu Tyr Gln Val
     50                  55                  60

Leu Asp Gly Ala Gly Leu Asp Ile Asp Phe His Leu Ala Ser Pro Glu
65                   70                  75                  80

Gly Lys Thr Leu Val Phe Glu Gln Arg Lys Ser Asp Gly Val His Thr
                 85                  90                  95

Val Glu Thr Glu Val Gly Asp Tyr Met Phe Cys Phe Asp Asn Thr Phe
            100                 105                 110

Ser Thr Ile Ser Glu Lys Val Ile Phe Phe Glu Leu Ile Leu Asp Asn
            115                 120                 125

Met Gly Glu Gln Ala Gln Glu Gln Asp Trp Lys Lys Tyr Ile Thr
            130                 135                 140

Gly Thr Asp Ile Leu Asp Met Lys Leu Glu Asp Ile Leu Glu Ser Ile
145                 150                 155                 160

Asn Ser Ile Lys Ser Arg Leu Ser Lys Ser Gly His Ile Gln Ile Leu
                165                 170                 175
```

Leu Arg Ala Phe Glu Ala Arg Asp Arg Asn Ile Gln Glu Ser Asn Phe
        180                 185                 190

Asp Arg Val Asn Phe Trp Ser Met Val Asn Leu Val Val Met Val Val
    195                 200                 205

Val Ser Ala Ile Gln Val Tyr Met Leu Lys Ser Leu Phe Glu Asp Lys
    210                 215                 220

Arg Lys Ser Arg Thr
25

(2) INFORMATION FOR SEQ ID NO: 4:

(i) SEQUENCE CHARACTERISTICS:
        (A) LENGTH: 892 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO: 4:

```
CGGCTCGAGC GAGGAGTCCA GAGAGGAAAC GCGGANGAGG ACAACAGTAC CTGACGCCTC      60

TTTCAGCCCG GGATCGCCCC AGCAGGGATG GGCGACAAGA TCTGGCTGCC CTTCCCCGTG     120

CTCCTTCTGG CCGCTCTGCC TCCGGTGCTG CTGCCTGGGG CGGCCGGCTT CACACCTTCC     180

CTCGATAGCG ACTTCACCTT TACCCTTCCC GCCGGCCAGA AGGAGTGCTT CTACCAGCCC     240

ATGCCCCTGA AGGCCTCGCT GGAGATCGAG TACCAAGTTT TAGATGGAGC AGGATTAGAT     300

ATTGATTTCC ATCTTGCCTC TCCAGAAGGC AAAACCTTAG TTTTTGAACA AGAAAATCA      360

GATGGAGTTC ACACTGTAGA GACTGAAGTT GGTGATTACA TGTTCTGCTT TGACAATACA     420

TTCAGCACCA TTTCTGAGAA GGTGATTTTC TTTGAATTAA TCCTGGATAA TATGGGAGAA     480

CAGGCACAAG AACAAGAAGA TTGGAAGAAA TATATTACTG GCACAGATAT ATTGGATATG     540

AAACTGGAAG ACATCCTGGA ATCCATCAAC AGCATCAAGT CCAGACTAAG CAAAAGTGGG     600

CACATACAAA TTCTGCTTAG AGCATTTGAA GCTCGTGATC GAAACATACA AGAAAGCAAC     660

TTTGATAGAG TCAATTTCTG GTCTATGGTT AATTTAGTGG TCATGGTGGT GGTGTCAGCC     720

ATTCAAGTTT ATATGCTGAA GAGTCTGTTT GAAGATAAGA GGAAAAGTAG AACTTAAAAC     780

TCCAAACTAG AGTACGTAAC ATTGAAAAAT GAGGCATAAA AATGCAATAA ACTGTTACAG     840

TCAAGACCAT TAATGGTCTT CTCCAAAATA TTTTGAGATA TAAAAGTAGG GC              892
```

(2) INFORMATION FOR SEQ ID NO: 5:

(i) SEQUENCE CHARACTERISTICS:
        (A) LENGTH: 227 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1223890

(xi) SEQUENCE DESCRIPTION: SEQ ID NO: 5:

Met Met Ala Ala Gly Ala Ala Leu Ala Leu Ala Leu Trp Leu Leu Met
1               5                   10                  15

Pro Pro Val Glu Val Gly Gly Ala Gly Pro Pro Ile Gln Asp Gly
            20                  25                  30

```
Glu Phe Thr Phe Leu Leu Pro Ala Gly Arg Lys Gln Cys Phe Tyr Gln
         35                  40                  45

Ser Ala Pro Ala Asn Ala Ser Leu Glu Thr Glu Tyr Gln Val Ile Gly
     50                  55                  60

Gly Ala Gly Leu Asp Val Asp Phe Thr Leu Glu Ser Pro Gln Gly Val
 65                  70                  75                  80

Leu Leu Val Ser Glu Ser Arg Lys Ala Asp Gly Val His Thr Val Glu
                 85                  90                  95

Pro Thr Glu Ala Gly Asp Tyr Lys Leu Cys Phe Asp Asn Ser Phe Ser
                100                 105                 110

Thr Ile Ser Glu Lys Leu Val Phe Phe Glu Leu Ile Phe Asp Ser Leu
            115                 120                 125

Gln Asp Asp Glu Glu Val Glu Gly Trp Ala Glu Ala Val Glu Pro Glu
        130                 135                 140

Glu Met Leu Asp Val Lys Met Glu Asp Ile Lys Glu Ser Ile Glu Thr
145                 150                 155                 160

Met Arg Thr Arg Leu Glu Arg Ser Ile Gln Met Leu Thr Leu Leu Arg
                165                 170                 175

Ala Phe Glu Ala Arg Asp Arg Asn Leu Gln Glu Gly Asn Leu Glu Arg
                180                 185                 190

Val Asn Phe Trp Ser Ala Val Asn Val Ala Val Leu Leu Leu Val Ala
            195                 200                 205

Val Leu Gln Val Cys Thr Leu Lys Arg Phe Pro Gln Asp Lys Arg Pro
    210                 215                 220

Val Pro Thr
225

(2) INFORMATION FOR SEQ ID NO: 6:

(i) SEQUENCE CHARACTERISTICS:
        (A) LENGTH: 201 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1212965

(xi) SEQUENCE DESCRIPTION: SEQ ID NO: 6:

Met Val Thr Leu Ala Glu Leu Leu Val Leu Leu Ala Ala Leu Leu Ala
 1               5                  10                  15

Thr Val Ser Gly Tyr Phe Val Ser Ile Asp Ala His Ala Glu Glu Cys
             20                  25                  30

Phe Phe Glu Arg Val Thr Ser Gly Thr Lys Met Gly Leu Ile Phe Glu
         35                  40                  45

Val Ala Glu Gly Gly Phe Leu Asp Ile Asp Val Glu Ile Thr Gly Pro
     50                  55                  60

Asp Asn Lys Gly Ile Tyr Lys Gly Asp Arg Glu Ser Ser Gly Lys Tyr
 65                  70                  75                  80

Thr Phe Ala Ala His Met Asp Gly Thr Tyr Lys Phe Cys Phe Ser Asn
                 85                  90                  95

Arg Met Ser Thr Met Thr Pro Lys Ile Val Met Phe Thr Ile Asp Ile
                100                 105                 110

Gly Glu Ala Pro Lys Gly Gln Asp Met Glu Thr Glu Ala His Gln Asn
            115                 120                 125

Lys Leu Glu Glu Met Ile Asn Glu Leu Ala Val Ala Met Thr Ala Val
```

130                 135                 140
Lys His Glu Gln Glu Tyr Met Glu Val Arg Glu Ile His Arg Ala
145                 150                 155                 160

Ile Asn Asp Asn Thr Asn Ser Arg Val Val Leu Trp Ser Phe Phe Glu
                165                 170                 175

Ala Leu Val Leu Val Ala Met Thr Leu Gly Gln Ile Tyr Tyr Leu Lys
            180                 185                 190

Arg Phe Phe Glu Val Arg Arg Val Val
            195                 200

(2) INFORMATION FOR SEQ ID NO: 7:

(i) SEQUENCE CHARACTERISTICS:
        (A) LENGTH: 201 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1213221

(xi) SEQUENCE DESCRIPTION: SEQ ID NO: 7:

Met Val Thr Leu Ala Glu Leu Leu Val Leu Leu Ala Ala Leu Leu Ala
1               5                   10                  15

Thr Ala Ser Gly Tyr Phe Val Ser Ile Asp Ala His Ala Glu Glu Cys
                20                  25                  30

Phe Phe Glu Arg Val Thr Ser Gly Thr Lys Met Gly Leu Ile Phe Glu
            35                  40                  45

Val Ala Glu Gly Gly Phe Leu Asp Ile Asp Val Glu Ile Thr Gly Pro
50                  55                  60

Asp Asn Lys Gly Ile Tyr Lys Gly Asp Arg Glu Ser Ser Gly Lys Tyr
65                  70                  75                  80

Thr Phe Ala Ala His Met Asp Gly Thr Tyr Lys Phe Cys Phe Ser Asn
                85                  90                  95

Arg Met Ser Thr Met Thr Pro Lys Ile Val Met Phe Thr Ile Asp Ile
            100                 105                 110

Gly Glu Ala Pro Lys Gly Gln Asp Met Glu Thr Glu Ala His Gln Asn
            115                 120                 125

Lys Leu Glu Glu Met Ile Asn Glu Leu Ala Val Ala Met Thr Ala Val
130                 135                 140

Lys His Glu Gln Glu Tyr Met Glu Val Arg Glu Arg Ile His Arg Ala
145                 150                 155                 160

Ile Asn Asp Asn Thr Asn Ser Arg Val Val Leu Trp Ser Phe Phe Glu
                165                 170                 175

Ala Leu Val Leu Val Ala Met Thr Leu Gly Gln Ile Tyr Tyr Leu Lys
            180                 185                 190

Arg Phe Phe Glu Val Arg Arg Val Val
            195                 200

(2) INFORMATION FOR SEQ ID NO: 8:

(i) SEQUENCE CHARACTERISTICS:
        (A) LENGTH: 203 amino acids
        (B) TYPE: amino acid
        (C) STRANDEDNESS: single
        (D) TOPOLOGY: linear (vii) IMMEDIATE SOURCE:
        (A) LIBRARY: GenBank -continued

```
    (B) CLONE: 417435

(xi) SEQUENCE DESCRIPTION: SEQ ID NO: 8:

Met Ala Ser Phe Ala Thr Lys Phe Val Ile Ala Cys Phe Leu Phe Phe
1               5                   10                  15

Ser Ala Ser Ala His Asn Val Leu Leu Pro Ala Tyr Gly Arg Arg Cys
                20                  25                  30

Phe Phe Glu Asp Leu Ser Lys Gly Asp Glu Leu Ser Ile Ser Phe Gln
            35                  40                  45

Phe Gly Asp Arg Asn Pro Gln Ser Ser Ser Gln Leu Thr Gly Asp Phe
        50                  55                  60

Ile Ile Tyr Gly Pro Glu Arg His Glu Val Leu Lys Thr Val Arg Asp
65              70                  75                  80

Thr Ser His Gly Glu Ile Thr Leu Ser Ala Pro Tyr Lys Gly His Phe
                85                  90                  95

Gln Tyr Cys Phe Leu Asn Glu Asn Thr Gly Ile Glu Thr Lys Asp Val
            100                 105                 110

Thr Phe Asn Ile His Gly Val Val Tyr Val Asp Leu Asp Asp Pro Asn
            115                 120                 125

Thr Asn Thr Leu Asp Ser Ala Val Arg Lys Leu Ser Lys Leu Thr Arg
        130                 135                 140

Glu Val Lys Asp Glu Gln Ser Tyr Ile Val Ile Arg Glu Arg Thr His
145                 150                 155                 160

Arg Asn Thr Ala Glu Ser Thr Asn Asp Arg Val Lys Trp Trp Ser Ile
                165                 170                 175

Phe Gln Leu Gly Val Val Ile Ala Asn Ser Leu Phe Gln Ile Tyr Tyr
            180                 185                 190

Leu Arg Arg Phe Phe Glu Val Thr Ser Leu Val
            195                 200
```